United States Patent [19]

Coughlan et al.

[11] Patent Number: 4,564,010
[45] Date of Patent: Jan. 14, 1986

[54] PRESSURE SENSITIVE ADHESIVE FILM FOR MEDICAL USE

[75] Inventors: Raymond T. Coughlan, Darien; Terrence J. Anderson, Chicago, both of Ill.

[73] Assignee: Daubert Coated Products Inc., Chicago, Ill.

[21] Appl. No.: 601,708

[22] Filed: Apr. 18, 1984

[51] Int. Cl.$^4$ .......................... A61L 15/00; B32B 7/10
[52] U.S. Cl. .................................. 128/156; 604/307; 604/896; 428/355
[58] Field of Search ....................... 604/896, 307, 304; 428/343, 351, 355; 128/156

[56] References Cited

U.S. PATENT DOCUMENTS

| | | | |
|---|---|---|---|
| 3,598,123 | 8/1971 | Zaffaroni | 604/304 |
| 4,484,574 | 11/1984 | DeRusha et al. | 128/156 |
| 4,485,087 | 11/1984 | Otsuka et al. | 604/896 |
| 4,485,809 | 12/1984 | Dellas | 604/307 |
| 4,492,724 | 1/1985 | Allbright et al. | 428/355 |

FOREIGN PATENT DOCUMENTS 930668  7/1973  Canada ............................ 604/304

Primary Examiner—Howard S. Williams
Attorney, Agent, or Firm—Wallenstein, Wagner, Hattis, Strampel & Aubel

[57] ABSTRACT

Pressure sensitive adhesive film having special utility for maintaining medical devices on the human skin. The film comprises a laminated base layer on a surface of which a water based pressure sensitive adhesive is coated. The adhesive is formed of a mixture of a polyacrylic latex and an ester resin, together with a thickening agent.

11 Claims, 8 Drawing Figures

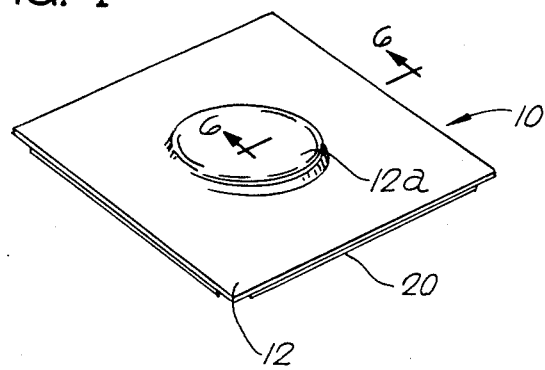
FIG. 1
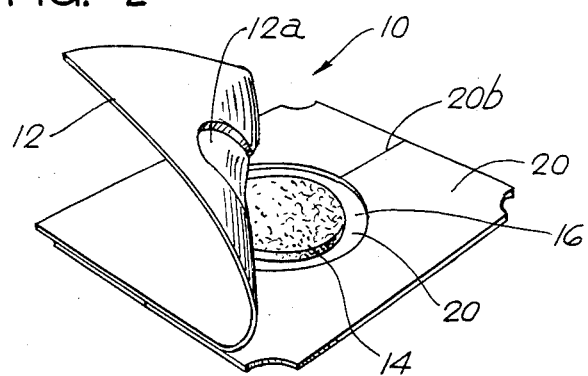
FIG. 2
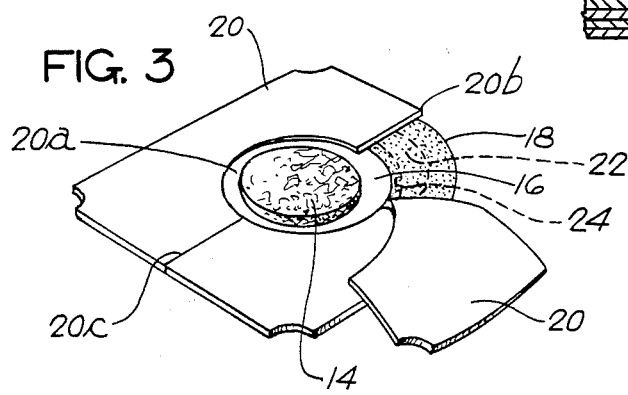
FIG. 3
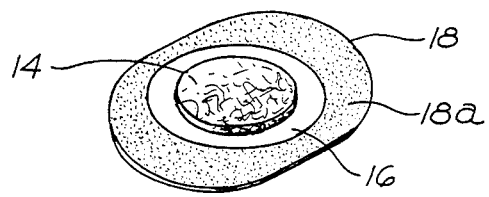
FIG. 4
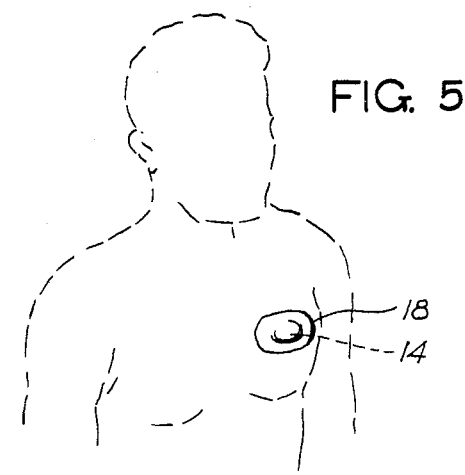
FIG. 5
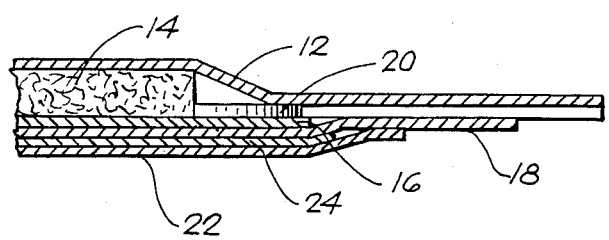
FIG. 6
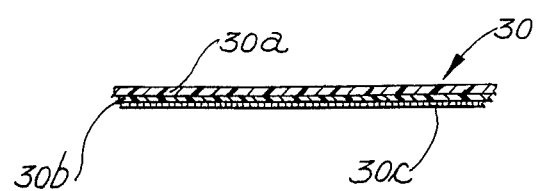
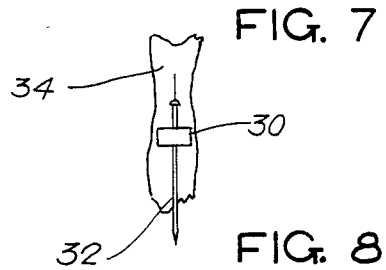
FIG. 7
FIG. 8

PRESSURE SENSITIVE ADHESIVE FILM FOR MEDICAL USE

TECHNICAL FIELD

The present invention relates to pressure sensitive adhesive films, and, in particular to pressure sensitive adhesive films for maintaining a medical device on the skin of a person while the device is in use.

BACKGROUND OF THE INVENTION

Pressure sensitive adhesive coated plastic film materials have, in the past, been used for attaching a variety of medical devices, including ostomy appliances and intravenous tubes, to the human body. More recently, such films have been used as a component in transdermal delivery systems which are placed in direct in contact with the skin of a patient while the drug or medicament carried by the device slowly passes through the skin and into the blood stream of the patient. One such device comprises a matrix infused with nitroglycerin in an inert vehicle consisting of water and glycerin for use in treating patients suffering from angina pectoris.

Film materials heretofore used for attaching and maintaining medical devices on human skin comprise polyethylene sheet material provided with an organic solvent coated layer of a pressure sensitive adhesive. Exemplary of one such film is a 3 mil polyethylene film coated with an organic solvent soluble acrylic adhesive. Apart from the unfavorable cost and environmental factors associated with the use of organic solvent coated pressure sensitive adhesives, their exists the potential for retention of a portion of the organic solvent in the final product. This residual solvent not only can result in irritation to the skin, but, also, can contaminate, and even react with, the drug or medicament carried by a medical device such as a transdermal bandage.

SUMMARY OF THE INVENTION

In accordance with the present invention, pressure sensitive adhesive films for medical use have been evolved which eliminate all of the aforementioned problems encountered with films utilizing an organic solvent coated pressure sensitive adhesive layer for adhering a medical device on human skin, whether the device be an ostomy appliance, an IV tube, or a transdermal drug delivery system. The films of the present invention are characterized both by their ability to withstand high humidity conditions, including skin perspiration, and, in the case of transdermal systems, by their inertness to a drug or medicament such as nitroglycerin and the vehicle in which it is carried, or, in the case of ostomy appliances, to body fluids. The excellent tolerance of the films to moisture, and their resistance to any detackifying effects caused by chemicals comprising the drug or medicament and its vehicle, enable a medical device to be maintained on a desired area of the human skin for an optimum period of time. What is more, these results are achieved without irritation to the human skin.

The pressure sensitive adhesive films of the present invention, in brief, comprise laminar structures which include a thin, flexible laminated base layer which advantageously is formed of a coextruded layer of a polyolefin and a layer composed of a mixture of polyolefin and a copolymer of ethylene and a vinyl ester. A layer of a water based pressure sensitive adhesive consisting essentially of a major proportion of a water-insoluble polyacrylic latex and a minor proportion of a water-insoluble ester resin, is coated on the polyethylene-copolymer layer. A small amount of a thickening agent desirably is incorporated into the water based adhesive mixture. Standard equipment and techniques can be employed in forming the pressure sensitive adhesive coating on the plastic films.

The foregoing, and other features and advantages of the invention will become more apparent from the description to follow, taken in conjunction with the accompanying drawings.

BRIEF DESCRIPTION OF THE DRAWINGS

FIG. 1 is a view in perspective of a transdermal medical device of the type employing a pressure sensitive adhesive film of the present invention;

FIG. 2 is a view in perspective of the device shown in FIG. 1 with the upper, protective layer of the device partly removed to expose the drug or medicament impregnated pad;

FIG. 3 is a view in perspective of the device shown in FIG. 1 with the upper, protective layer completely removed, and the release coated liner being separated from the pressure sensitive adhesive nonwoven tape;

FIG. 4 is a view in perspective of the bandage comprising the device shown in FIG. 1 ready to be applied on the skin of a patient;

FIG. 5 is a schematic representation of the bandage shown in FIG. 4 attached to the chest area of a patient; and FIG. 6 is an enlarged sectional view taken substantially along line 6—6 of FIG. 1;

FIG. 7 is an enlarged sectional view of a tape formed from the film of this invention; and FIG. 8 is a schematic represention of a tape such as is illustrated in FIG. 7 being used to secure an IV tube on the arm of a patient.

DETAILED DESCRIPTION OF THE INVENTION

The polyolefin used in forming the laminated base layer of the pressure sensitive adhesive films of the present invention desirably is a low or medium density polyethylene. Because of the desired flexibility, particularly preferred are polyethylenes having a density in the range of about 0.91 to about 0.94, especially about 0.922 to about 0.932. In those instances where the finished adhesive film is to be used as a component of a transdermal drug delivery system, the thickness of the polyethylene layer of the laminated structure can vary from about 1 mil to about 5 mils, with a thickness of the order of about 1.7 to about 2.1 mils being preferred. In those cases where the finished film is to be used as a tape to secure medical devices such as an IV tube on the skin of a patient, the polyethylene layer can have a thickness of about 2 to about 5, preferably about 3, mils.

The polyethylene employed in admixture with the ethylene-vinyl ester copolymer to form the second layer of the laminated base layer also desirably is a low or medium density polyethylene. The vinyl ester moiety of the ethylene-vinyl ester copolymer comprising the resin mixture may be selected from such vinyl esters as vinyl acetate, vinyl propionate and vinyl isobutyrate. Of this group, the preferred ester is vinyl acetate. The generally optimum objectives of the invention are attained with a mixture containing about 75% to about 90% by weight of polyethylene and about 25% to about 10% by weight of the ethylene-vinyl ester copolymer. The copolymer may contain about 20 to 60 mole percent ethylene and about 80 to 40 mole percent of vinyl ester. The thickness of the layer formed from the mixture of resins can range from about 0.2 mil to about 1 mil, preferably about 0.3 to about 0.5 mil.

The laminated base layer can be produced in various ways. Thus, for example, individual layers can be formed from the polyethylene, and the mixture of polyethylene and the copolymer, and combined in a conventional laminating operation. A particularly convenient and preferred method of producing the base layer involves the simultaneous extrusion of the polyethylene, and the mixture of resins, as a laminar extrudate through a single die slot. Generally, the degree of natural adhesion between the layers comprising the base layer, resulting from the coextrusion, is sufficient to prevent delamination of the base layer in use.

The water based pressure sensitive adhesive layer which, as stated, is coated on the layer of the laminated base layer formed from the mixture of polyethylene and the ethylene-vinyl ester copolymer consists essentially of a water-insoluble polyacrylic latex and a water-insoluble ester resin. The polyacrylic latex advantageously should comprise about 70 to about 85, usually about 75 to about 78, parts by weight of the adhesive layer. The ester resin desirably should comprise about 30 to about 15, preferably about 20 or 22, parts by weight of the adhesive. The properties of the adhesive can be enhanced by adding a small amount, usually about 0.1 to about 1, preferably about 0.4 to about 0.6, parts by weight of a thickening agent to the adhesive layer forming mixture.

While a number of commercially available polyacrylic latex products can be used for the purposes of this invention, an especially preferred product is the one sold under the designation HYCAR 2600X222 (B. F. Goodrich). HYCAR 2600X222 is a polyacrylic latex namely, an acrylic ester copolymer containing ethyl hexylacrylate and acrylamide, in the form of a colloidal suspension of individual, generally spherical polymer particles in water. The percent total solids of the suspension is in the range of 49.5 to 52.5, and the Brookfield viscosity of the suspension, at 25° C., 49.5 total solids, is about 30 to 150 cps. Also useful are high solids (62%–65%) aqueous acrylic emulsions available commercially under the designations "GELVA" multipolymer emulsions RA-2474 and RA-2397 (Monsanto). A preferred composition comprises a 50—50 mixture of RA-2474 AND RA-2397.

The ester resin, similarly, can be selected from a number of commercially available products. A preferred product for the purposes of this invention is the product sold under the designation FORAL 105 (Hercules Incorporated). This ester resin is derived from pentaerythritol and a highly stabilized rosin.

The thickening agents which can be used in forming the adhesive layer include various acrylic polymers and polymerized metal salts of acrylic acid. Exemplary of suitable thickening agents are the acrylic polymer sold under the designation ACRYSOL ASE-60 (Rohm and Haas Company), and the sodium polyacrylate sold by the same company under the designation ACRYSOL GS.

The thickness of the pressure sensitive adhesive layer carried on the laminated base layer is variable. The generally optimum objectives of the invention are attained with adhesive layer thicknesses of the order of about 1 to 2.5 mils, preferably about 1.5 to about 2 mils. The adhesive can be applied with standard equipment using conventional water based pressure sensitive adhesive coating techniques.

Referring, now, in greater detail to FIGS. 1–6 of the drawings, an embodiment of a transdermal medical device utilizing the film of this invention as a component is illustrated. The device, designated generally by reference numeral 10 incorporates, as an essential component of its construction, a pressure sensitive adhesive film of this invention which prevents body fluids, principally perspiration, and the vehicle for the drug or medicament from flowing through and/or staining the patient's clothing. The device is maintained on the skin of a patient as represented in FIG. 5. As shown, the device 10 includes an upper, protective, water impermeable layer 12 which may be fabricated of a plastic coated metal foil. The layer 12 is provided with a raised, central portion 12a which overlies a soft, flexible, circular bandage, or matrix 14. The matrix 14 comprises a drug or medicament carried in an inert vehicle. In the embodiment illustrated, the drug or medicament is nitroglycerin, and the vehicle is a mixture of water and glycerin. In forming the matrix 14, the drug or medicament is mixed with the components comprising the inert vehicle. The resulting mixture is then extruded into roll-like form and is thereafter sliced to provide a matrix of desired thickness. In the embodiment of the device 10 shown, the matrix 14 can vary in thickness from about ⅛ inch to about ½ inch, preferably about ¼ inch.

The matrix 14 is lightly adhered to a water impermeable foil disc 16 which, in turn, is adhered to the pressure sensitive adhesive layer of a generally oval shaped nonwoven sheet 18. A release coated liner 20, provided with a centrally located opening 20a therethrough, is positioned between the upper layer 12 and the adhesive layer of the sheet 18. The liner 20 is slit as at 20b and 20c to facilitate its removal from the adhesive layer of the sheet 18. Removal of the liner 20 exposes peripheral areas 18a of the adhesive layer of the sheet 18 which serves to maintain the bandage or matrix 14 in contact with the skin of a patient until the drug or medicament is exhausted, or no longer required. A backing layer 22, which carries a circular scrim reinforced tissue pad 24 on its inner surface, is adhered to the outer surface of the nonwoven sheet 18.

It should be understood that the foregoing description of the device 10 is for illustrative purposes only, and that the pressure sensitive adhesive film of this invention can be used with other medical devices. Thus, as illustrative in FIGS. 7 and 8, an embodiment of the medical adhesive film of this invention is shown being used as a tape 30 to secure an IV tube 32 on the arm 34 of a patient. The tape 30, illustrated in enlarged cross-section in FIG. 7, comprises a polyethylene layer 30a to which is laminated a polyethylene-ethylene-vinyl ester copolymer (EVA) layer 30b. A water based pressure sensitive layer 30c is, in turn, coated on the copolymer layer 30b. A release coated liner, not shown, is applied to the adhesive layer 30c to protect it prior to applying the tape to a patient's skin.

The following examples are illustrative of the present invention. The numerical values are in weight percent.

EXAMPLE 1

A water based pressure sensitive adhesive composition was prepared using the following ingredients:

| Ingredient | Percent |
| --- | --- |
| Polyacrylic latex (HYCAR 2600X222) | 78.1 |
| Ester resin (FORAL 105) | 21.3 |
| Thickening agent (ACRYSOL GS) | 0.6 |

The resulting aqueous composition was roller coated on the EVA side of a laminated base layer formed from coextruded polyethylene and a mixture of polyethylene and an ethylene-vinyl acetate copolymer (EVA). The adhesive layer was then dried. A 1"×6" strip of the resulting film was laminated to 3M 1530 nonwoven sheet material using a 4½ lb. roller. After one minute, the laminate was immersed in 37° C. water for one hour. The sample was then removed from the water and blot dried. The force required to remove the film strip from the laminate was then determined. The film strip began to separate under a load of 600 grams. No adhesive was removed from the film strip. This same test performed on a polyethylene film without the EVA layer resulted in stripping forces of 100 grams and all the adhesive transferred from the film.

EXAMPLE 2

A water based pressure sensitive adhesive composition was prepared using the following ingredients:

| Ingredient | Percent |
| --- | --- |
| Polyacrylic latex (HYCAR 2600X222) | 80.3 |
| Ester resin (FORAL 105) | 19.1 |
| Thickening agent (ACRYSOL ASE-60) | 0.6 |

The composition was coated on a laminated base layer and tested as in Example 1. The film strip began to separate under a load of 580 grams. No adhesive was removed from the film strip during separation.

What is claimed is:

1. A pressure sensitive adhesive film for securing a medical device on human skin, comprising: a base layer in the form of a laminate, one layer of which is formed of a polyolefin and another layer of which is formed of a mixture of a polyolefin and an ethylene-vinyl ester copolymer; and a layer of a water base coated pressure sensitive adhesive on the surface of the layer of said laminate which is formed of said copolymer, said water base coated pressure sensitive adhesive layer consisting essentially of a mixture of a water-insoluble polyacylic latex and a water-insoluble ester resin, and being characterized in that it is water and perspiration resistant and inert with respect to drugs or medicaments with which it may come into contact with while securing a medical device on human skin, and further being characterized in that it is non-irritating to the human skin.

2. A film according to claim 1 wherein the polyacrylic latex comprises about 70% to about 85% by weight of the adhesive layer.

3. A film according to claim 1 wherein the ester resin comprises about 15% to about 30% by weight of the adhesive layer.

4. A film according to claim 1 wherein the adhesive layer includes a thickening agent in the form of an acrylic polymer or a metal salt of an acrylic acid.

5. In a transdermal delivery system which includes an element for carrying a drug or medicament adapted to be absorbed into the body through the human skin, the improvement which comprises as a component of said system: a film in the form of a laminate, one layer of which is formed of a polyolefin and another layer of which is formed of a mixture of a polyolefin and an ethylene-vinyl ester copolymer; and a layer of a water based coated pressure sensitive adhesive on the surface of the layer of said film which is formed of said copolymer, said pressure sensitive adhesive layer consisting essentially of a mixture of a water-insoluble polyacrylic latex and a water-insoluble ester resin, and being characterized in that it is water and perspiration resistant and substantially inert with respect to the drug or medicament carried by said element, and, further, in that it is non-irritating to the human skin.

6. In a medical device according to claim 5 wherein a thickening agent is incorporated in the pressure sensitive adhesive layer.

7. In a medical device according to claim 6 wherein the thickening agent is an acrylic polymer or a metal salt of an acrylic acid.

8. In a medical device according to claim 7 wherein the thickening agent comprises about 1% to about 2% by weight of the adhesive layer.

9. In a medical device according to claim 5 wherein the polyacrylic latex comprises about 70% to about 85% by weight of the adhesive layer.

10. In a medical device according to claim 5 wherein the ester resin comprises about 15% to about 30% by weight of the adhesive layer.

11. In a medical device according to claim 5 wherein the film is formed of a layer of polyethylene and a layer formed from a mixture of polyethylene and an ethylene-vinyl ester copolymer.

* * * * *